United States Patent [19]

Keim et al.

[11] Patent Number: 4,554,388

[45] Date of Patent: Nov. 19, 1985

[54] PROCESS FOR ISOMERIZATION AND TRANSALKYLATION OF ALKYLPHENOLS

[75] Inventors: Karl-Heinz Keim, Heimerzheim; Joachim Korff, Bornheim-Merten, both of Fed. Rep. of Germany

[73] Assignee: Rheinische Braunkohlenwerke Aktiengesellschaft, Cologne, Fed. Rep. of Germany

[21] Appl. No.: 577,849

[22] Filed: Feb. 7, 1984

[30] Foreign Application Priority Data

Feb. 11, 1983 [DE] Fed. Rep. of Germany ....... 3304663

[51] Int. Cl.$^4$ .................................. C07C 39/07
[52] U.S. Cl. ............................ 568/716; 568/780; 568/783; 568/790; 568/794
[58] Field of Search ............ 568/716, 783, 780, 790, 568/794

[56] References Cited

U.S. PATENT DOCUMENTS

| 3,519,692 | 7/1970 | Hess | 568/783 |
| 3,933,927 | 1/1976 | Goddard | 568/716 |
| 4,398,048 | 8/1983 | Firth | 568/794 |

FOREIGN PATENT DOCUMENTS

| 0039525 | 11/1970 | Japan | 568/783 |
| 0789482 | 11/1980 | Japan | 568/716 |
| 695464 | 8/1953 | United Kingdom | 568/783 |

*Primary Examiner*—Werren B. Lone
*Attorney, Agent, or Firm*—Connolly and Hutz

[57] ABSTRACT

This invention relates to a process for isomerization and transalkylation of alkylphenols and for phenol-derivatives in the presence of a catalyst comprising ironoxide (s) and at least one additional oxide and in the case of 2,4,6-trimethylphenol and 2,4-dimethylphenol as alkylphenol feed, of ironoxide (s) or of a catalyst comprising ironoxide (s) and at least one additional oxide.

10 Claims, No Drawings

PROCESS FOR ISOMERIZATION AND TRANSALKYLATION OF ALKYLPHENOLS

BACKGROUND OF THE INVENTION (1) Field of the Invention

This invention relates to a process for isomerization and transalkylation of alkylphenols and for phenolderivatives in the presence of a catalyst comprising ironoxide (s) and at least one additional oxide and in the case of 2,4,6-trimethylphenol and 2,4-dimethylphenol as alkylphenol feed, of ironoxide (s) or of a catalyst comprising ironoxide (s) and at least one additional oxide.

(2) Description of the Prior Art

Isomerization and transalkylation of alkylphenols in the presence of acidic catalysts are known for a long time. GB-PS No. 695 464 discloses a process in which the use of aluminum silicate and of mixed oxides of silicon, beryllium, magnesium, aluminum, zirconium and titanium for isomerizations and transalkylations of alkylphenols is described.

In DE-OS No. 18 04 632 isomerizations and transalkylations are disclosed with mixed catalysts consisting of alumina and silicic acid.

The known processes however are not satisfactory with regard to technical scale operation, since the conversion to desirable products from an economical point of view, for example to monoalkylphenols, 2,6-resp. 2,4-dimethylphenol or 2,3,6-trimethylphenol is relatively low. This is also the case if alkylphenols comprising several alkyl groups, are converted in the presence of phenol.

Effective, technically useful catalysts, which permit the isomerization and transalkylation of alkylphenols with up to five alkyl groups and alkylphenols mixtures, which additionally contain residues originating from technical units, in the presence of relatively small amounts of added phenol in order to obtain useful products are not known. With the catalysts of the state of the art only negligible amounts of residues are converted to desirable products.

SUMMARY OF THE INVENTION

According to the present invention, a process has been found for isomerization and transalkylation of alkylphenols and/or phenol derivatives b reacting the alkylphenols and/or phenol derivatives, optionally in the presence of phenol, at temperatures of 200°-550° C., pressures of 1-300 bar (at reaction temperature) and residence times of 0,1-10 hours in the presence of metal oxides as catalyst, characterized in that the process is carried out in the presence of (a) iron oxide (s)
(b) at least one oxide selected from the groups consisting of
  1. B, Al, Ce
  2. Si, Ge, Sn, Ti, Zr
  3. Cr, V
  4. Li, Na, K, Rb, Cs, Be, Mg, Ca, Sr, Ba, Mn, La.

Furthermore a process has been found for isomerization and transalkylation of 2,4,6-trimethylphenol and/or 2,4-dimethylphenol by reacting these alkylphenols in the presence of phenol and/or alkylated phenols at temperatures of 200°-550° C., pressures of 1-300 bar (at reaction temperature) and residence times of 0,1-10 hours in the presence of metal oxide (s), characterized in that the process is carried out in the presence of a catalyst consisting of iron oxide (s) or of a catalyst consisting of iron oxide (s) and at least one oxide selected from the groups consisting of 1. B, Al, Ce, Ga, In, Sc, Y
2. Si, Ge, Sn, Pb, Ti, Zr, Hf
3. Cr, V, Nb, Ta, Mo, W, Re, Co, Ni, Ru, Ir
4. Li, Na K, Rb, Cs, Be, Mg, Ca, Sr, Ba, Mn, La, Ca, Zn, Cd

DESCRIPTION OF THE PREFERRED EMBODIMENTS

Preferred reaction conditions are 250°-450° C., 10-150 bar (at reaction temperature) and residence times of 0,5-7 hrs. The reaction can be carried out continuously or discontinuously. Useful technical reactors are tubular reactors, the tubes of which are filled with pelletized or granular catalyst. However the catalyst can also be applied in different shapes. The inventive process can also be carried out in fluid bed systems, using a grinded catalyst. These procedures and devices are known to the artisan.

The investigations of applicant have shown that it is of advantage to work under inert gas pressure, for example in a hydrogen atmosphere, nitrogen, $CO_2$ or steam atmosphere. Thus addition of water can be advantageous.

The inventive isomerizations and transalkylations of alkylphenols and phenolderivatives are preferrentially carried out in the presence of phenol, but they can also be carried out in the presence of other added phenolderivatives, for example of cresols or anisol.

Although the reaction can be carried out in the gas phase, the liquid phase is generally preferred. Working up of the reaction product can be carried out by conventional separation processes like distillation, extraction and cristallyzation. The residue which remains after these separation procedures can be recycled to the isomerization and transalkylation process, leading to an almost complete conversion of the residue, optionally after having separated resinous material.

EXAMPLES AND TABLES

The following examples and tables illustrate the invention in more detail.

The examples of table 1 have been carried out with a catalyst consisting of $Fe_2O_3/SiO_2/Cr_2O_3/BaO$ with a $Fe_2O_3$-portion being higher than 90% by weight.

Residence time was 1-4 hours. As an inert gas, hydrogen was applied with a pressure of 1 and 30 bar (at normal temperature). Reaction temperature was 400° C. In the first line the feed is shown. In all examples a mixture of 20 weight-% of phenol and 80 weight percent of a mixture of methylphenols and residue of a technical phenol-alkylation unit was used. The residue was a product which could not be distilled at 190° C. and 3 mbar. 67,32 weight-% were methylated phenols with more than two methyl groups. The second column from the right side represents the total amount of desired, economically valuable mono- and dimethylphenols. The column at the right side represents the quantity of phenol consumed. As a whole (without added phenol) the feed was a residue taken from a technical phenol alkylation unit, from which mono- and dimethylphenols had been essentially distilled off.

The table shows that with the catalyst used, after a residence time of 4 hours, a product can be obtained, which consists of 41,62 weight-% of mono- and dialkylphenols (27,9 weight-% of mono-methyl phenols) accompagnied by a decrease of higher alkylphenols of 34,7 weight-% and of the residue of 40,8 weight-%. Comparable results are obtained, if anisol is added instead of phenol.

At a residence time of 1 hour and a hydrogen pressure of 30 bar, 33,63 weight-% of mono- and dialkylphenols (23,6 weight-% monomethylphenols) are obtained, accompagnied by a corresponding decrease of residue. At a residence time of 1 hour and 30 bar of hydrogen pressure, 33,71 weight-% of mono- and dimethylphenols are obtained.

table 1, where a residence time of 2 hours has been applied.

The result demonstrates that the quantity of mono- and dialkylphenols obtained, decreases from 38,64 weight-% (25,83 monomethylphenols) in the total product to 30,09 weight-% (20,2 weight-% monomethylphenols), accompagnied by an increase of non-distillable residue to 25,7 weight-%, whereby 73,25 weight-% of added phenol is consumed.

Also the use of $\gamma$-$Al_2O_3$ leads to a considerably lower yield with regard to mono- and dialkylphenols (18,56

TABLE 1

| catalyst | resicence time hrs | bar $H_2$ | Ph. feed | T °C. | Ph | o-cresol | m-cresol | p-cresol | 2,4-DMP | 2,6-DMP | higher methyl phenols | dist. residue | o-,m-,p-,Cr 2,4- and 2,6-DMP | phenol consumed |
|---|---|---|---|---|---|---|---|---|---|---|---|---|---|---|
| feed | | | | | 20,0 | 0,06 | 0,01 | 0,12 | 1,71 | 0,14 | 67,32 | 10,64 | 2,04 | — |
| $Fe_2O_2$:$SiO_2$ $Cr_2O_3$:BaO-100:2:1:1 | 1 | 1 | 20 | 400 | 7,83 | 11,56 | 7,58 | 4,07 | 7,22 | 3,28 | 43,36 | 15,1 | 33,71 | 60,85 |
| $Fe_2O_2$:$SiO_2$ $Cr_2O_3$:BaO-100:2:1:1 | 1 | 30 | 20 | 400 | 9,54 | 13,92 | 6,21 | 3,44 | 7,11 | 2,95 | 51,63 | 5,2 | 33,63 | 52,3 |
| $Fe_2O_2$:$SiO_2$ $Cr_2O_3$:BaO-100:2:1:1 | 2 | 30 | 20 | 400 | 8,04 | 13,23 | 8,17 | 4,43 | 8,47 | 4,34 | 47,12 | 6,2 | 38,64 | 59,8 |
| $Fe_2O_2$:$SiO_2$ $Cr_2O_3$:BaO-100:2:1:1 | 4 | 30 | 20 | 400 | 8,12 | 13,24 | 9,68 | 5,0 | 9,04 | 4,66 | 43,96 | 6,3 | 41,62 | 59,4 |
| $Fe_2O_2$:$SiO_2$ $Cr_2O_3$:BaO-100:2:1:1 | 2 | 50 | 20 | 400 | 8,85 | 14,38 | 6,87 | 3,64 | 7,87 | 3,35 | 52,24 | 2,8 | 36,11 | 55,75 |
| $Fe_2O_3$:$SiO_2$: $Cr_2O_3$:BaO | 2 | 50 | feed | 400 | anisol 21,2 | 0,05 | 0,01 | 0,11 | 1,70 | 0,13 | 66,87 | 9,93 | | — |
| | 2 | 50 | | 400 | phenol 8,84 | 14,41 | 7,01 | 3,68 | 7,93 | 3,36 | 52,13 | 2,64 | 36,39 | 55,46 |

Comparative examples are shown in table 2. with weight-% of monomethylphenols).

TABLE 2

| catalyst | resicence time hrs | bar $H_2$ | Ph. feed | T °C. | Ph | o-cresol | m-cresol | p-cresol | 2,4-DMP | 2,6-DMP | higher methyl phenols | dist. residue | o-,m-,p-,Cr 2,4-and 2,6-DMP | phenol consumed |
|---|---|---|---|---|---|---|---|---|---|---|---|---|---|---|
| white-pearls $Al_2O_3$, (10%) $SiO_2$ (90%) | 2 | 30 | 20 | 400 | 5,35 | 7,53 | 9,09 | 3,59 | 6,78 | 3,10 | 38,86 | 25,7 | 30,09 | 73,25 |
| $\alpha$-$Al_2O_3$ | 2 | 30 | 20 | 400 | 8,62 | 8,56 | 4,83 | 5,17 | 8,14 | 2,54 | 53,34 | 8,8 | 29,24 | 56,9 | conventional catalysts.

The example, carried out with so-called white pearls ($Al_2O_3$/$SiO_2$) is to be compared with the example of Table 3 shows examples with various inventive catalysts and as a comparative example the reaction with $Fe_3O_4$ as catalyst without addition of a further oxide.

The comparative example indicates the effect of an additional oxide.

TABLE 3

| catalyst | resicence time hrs | bar H$_2$ | Ph. feed | T °C. | Ph | o-cresol | m-cresol | p-cresol | 2,4-DMP | 2,6-DMP | higher methyl phenols | dist. residue | o-,m-,p-,Cr 2,4- and 2,6-DMP | phenol consumed |
|---|---|---|---|---|---|---|---|---|---|---|---|---|---|---|
| — | — | — | — | — | 20,0 | 0,06 | 0,01 | 0,12 | 1,71 | 0,14 | 67,32 | 10,64 | 2,04 | — |
| Fe$_2$O$_3$:SiO$_2$: Cr$_2$O$_3$:BaO 100:2:1:1 | 2 | 30 | | | 8,04 | 13,23 | 8,17 | 4,43 | 8,47 | 4,34 | 47,12 | 6,2 | 38,64 | 59,8 |
| Fe$_2$O$_3$:SiO$_2$: Cr$_2$O$_3$ 100:4:1 | 2 | 30 | | | 6,79 | 12,51 | 8,16 | 4,33 | 9,16 | 4,68 | 46,57 | 7,8 | 38,84 | 66,05 |
| Fe$_2$O$_3$:SiO$_2$: MnO:CaO 100:2:1:0,2 | 2 | 30 | | | 7,39 | 13,21 | 7,78 | 4,28 | 8,86 | 4,16 | 49,32 | 5,0 | 38,29 | 63,05 |
| Fe$_2$O$_3$:ZrO$_2$: Cr$_2$O$_3$:BaO 100:2:1:1 | 2 | 30 | | | 9,22 | 13,11 | 6,59 | 3,6 | 7,27 | 3,07 | 50,44 | 6,7 | 33,64 | 53,9 |
| Fe$_2$O$_3$:SiO$_2$: V$_2$O$_5$:BaO 100:2:1:0,2 | 2 | 30 | | | 7,99 | 13,12 | 6,76 | 3,78 | 7,56 | 3,6 | 46,69 | 10,5 | 34,82 | 60,05 |
| Fe$_3$O$_4$ | 2 | 30 | | | 16,33 | 7,31 | 3,25 | 2,77 | 6,07 | 1,54 | 55,33 | 7,4 | 20,94 | 18,35 |
| Fe$_2$O$_3$:SiO$_2$ 100:2 | 2 | 30 | | | 7,5 | 12,42 | 7,51 | 4,44 | 8,32 | 3,97 | 55,84 | 8,2 | 36,66 | 57,1 |

In table 4 experimental results are shown whereby the catalyst of table 1 has been used and the same conditions as indicated in table 1, with 2,4,6-trimethylphenol as feed and the addition of 22,2 weight-% of phenol. In a comparative experiment, Al$_2$O$_3$/SiO$_2$ (10/90 weight-%) was used. In both cases the reaction temperature was 370° C.

An example with 2,4,6-triethylphenol and 20 weight-% of added phenol is also shown in table 4.

The experiments have been carried out at 400° C., at a pressure of 30 bar (at normal temperature) and residence time of 2 hours.

The investigations of applicant have led to the result (not shown in the tables) that also at different temperatures, pressures and residence times, selectivities and very low quantities of residue are obtained.

The quantity of iron oxide (s) in the catalyst, generally amounted to at least 60 weight-%. Lower quantities

TABLE 4

| catalyst | resicence time hrs | bar H$_2$ | 2,4,6-TMP | pH | o-cresol | m-cresol | p-cresol | 2,4-DMP | 2,6-DMP | higher methyl phenols | dist. residue | o-,m-,p-,Cr 2,4- and 2,6-DMP | phenol consumed |
|---|---|---|---|---|---|---|---|---|---|---|---|---|---|
| | | | 2,4,6-TMP 370° C. | 77,1 | 22,2 | 0,1 | — | 0,05 | 0,61 | 0,02 | 0,02 | — | 0,69 | — |
| Fe$_2$O$_3$:SiO$_2$: Cr$_2$O$_3$:BaO 100:2:1:1 | 2 | 30 | 36,89 | 2,99 | 13,24 | — | 5,55 | 28,01 | 10,67 | 0,35 | 2,3 | 57,47 | 86,41 |
| white pearls | 2 | 30 | 25,76 | 2,75 | 6,44 | 5,36 | 3,46 | 10,52 | 4,98 | 27,23 | 13,5 | 30,76 | 87.5 |

| | 4,6-triethylphenol pure + 20 Gew. % phenol | phenol | o-ethylphenol | m-ethylphenol | p-ethylphenol |
|---|---|---|---|---|---|
| Fe$_2$O$_3$:SiO$_2$: Cr$_2$O$_3$:BaO 100:2:1:1 | 2   30 | 2,1 | 12,7 | — | 5,3 |

| | 2,4-diethylphenol | 2,6-diethylphenol | higher ethylphenlols | 2,4,6-triethylphenol |
|---|---|---|---|---|
| Fe$_2$O$_3$:SiO$_2$: Cr$_2$O$_3$:BaO 100:2:1:1 | 29,4 | 9,2 | 7,9 | 33,4 |

Furthermore investigations of applicant have shown that surprisingly and non-obvious to the artisan, with 2,4,6-trimethylphenol and 2,4-dimethylphenol as starting materials, not only combinations of iron oxide (s) with numerous additional oxides, but also iron oxide (s) alone lead to selective isomerizations and transalkylations, whereby in contrast to the state of the art no meta-substituted phenols are obtained, however very low quantities of residue.

Results according to the instant invention with iron oxide catalysts are shown in tables 5 (feed: 2,4,6-trimethylphenol) and 6 (2,4-dimethylphenol).

of iron oxide (s) lead to inferior results.

The ratio of phenol to alkylphenol was 50:50 weight-%. The quantities of products shown in the tables are specified in weight percent.

In table 5 a comparative experiment is shown with Al$_2$O$_3$/SiO$_2$ at catalyst.

The result shows that m-cresol, 2,5-dimethylphenol, 2,3-dimethylphenol and 2,3,6-trimethylphenol (all m-substituted) are formed. Furthermore 18,6 weight-% of residue were formed. Table 6 containes comparative examples with Al$_2$O$_3$/SiO$_2$ and a catalyst consisting of mixed oxides without iron oxide (s). This catalyst consisted predominantly of nickel oxide and small amounts of SiO$_2$, Cr$_2$O$_3$ and K$_2$O.

The examples of table 6 clearly demonstrate that in contrast to the inventive experiments neither selectivity nor the formation of only small amounts of residue are obtained.

The same results are obtained with regard to isomerization and transalkylation of 2,4,6-trimethylphenol and/or 2,4-dimethylphenol, if these compounds contain other alkylphenols in small amounts.

The abbreviations used in the tables are:
Ph=phenol
DMP=dimethylphenol
TMP=trimethylphenol
MP=methylphenols
Cr=cresols The experimental results summarized in the tables show the superiority of the catalysts used, according to the invention with respect to selective transformations to useful products combined with the formation of anly small amounts of residues.

In particular with 2,4,6-trimethylphenol and 2,4-dimethylphenol as feed, outstanding results are obtained.

What we claim is:

1. A process for the isomerization and transalkylation by catalytically reacting methylated or ethylated phenols and/or phenolderivatives in the presence of phenol at temperature of 200° to 550° C., pressures of 1 to 300 bar (at reaction temperature) and residence times of 0,1 to 10 hours in the presence of metal oxides as catalyst, characterized in that the process is carried out in the presence of a catalyst comprising
   (a) iron oxide (s)
   (b) at least one oxide selected from at least one of the groups
      1. B, Al, Ce
      2. Si, Ge, Sn, Ti, Zr
      3. Cr, V
      4. Li, Na, K, Rb, Cs, Be, Mg, Ca. Sr, Ba, Mn, La 2. A process for the isomerization and transalkylation by catalytically reacting 2,4,6-trimethylphenol and/or 2,4-dimethylphenol in the presence of phenol and/or alkylphenols at temperatures of 200°–550° C., pressures of 1 to 300 bar (at reaction temperature) and residence times of 0.1 to 10 hours in the presence of metal oxides

TABLE 5

| | | | | | | Product composition, weight-% | | | | | | | | |
|---|---|---|---|---|---|---|---|---|---|---|---|---|---|---|
| catalyst | Ph | o-cresol | m-cresol | p-cresol | 2,5-DMP | 2,4-DMP | 2,6-DMP | 2,3-DMP | resid. DMP | 2,4,6-TMP | 2,3,6-TMP | dist. resid. | o-,p-Cr; 3,4- and 3,6-DMP | phenol consumed |
| white pearls $SiO_2/Al_2O_3$ | 11,6 | 13,8 | 15,2 | 6,2 | 9,3 | 8,1 | 4,4 | 3,9 | 4,4 | 2,4 | 2,1 | 18,6 | 325 | 71,0 |
| $Fe_3O_4$ | 29,3 | 19,7 | — | 5,9 | — | 8,0 | 3,1 | — | — | 28,9 | — | 5,1 | 36,7 | 43,0 |
| $Fe_2O_3/Al_2O_3$ | 24,4 | 21,9 | — | 7,4 | — | 10,1 | 4,2 | — | — | 24,7 | — | 7,3 | 43,6 | 48,3 |
| $Fe_2O_3/Cr_2O_3/SiO_2/CaO$ | 26,7 | 20,1 | — | 7,8 | — | 15,5 | 5,1 | — | — | 22,4 | — | 2,4 | 48,5 | 46,6 |
| $Fe_2O_3/MoO_2 K_2O$ | 25,3 | 20,3 | — | 6,9 | — | 15,1 | 6,1 | — | — | 25,0 | — | 1,3 | 48,4 | 47,0 |
| $Fe_2O_3/V_2O_5$ | 26,0 | 18,9 | — | 6,4 | — | 14,7 | 5,4 | — | — | 25,1 | — | 3,5 | 45,4 | 45,9 |
| $Fe_2O_3/SnO_2/Na_2O$ | 27,4 | 19,7 | — | 7,1 | — | 15,0 | 6,2 | — | — | 23,6 | — | 1,0 | 48,0 | 44,9 |
| $Fe_2O_3/NiO GeO_2/K_2O$ | 25,9 | 20,1 | — | 7,2 | — | 15,0 | 6,4 | — | — | 24,5 | — | 0,9 | 48,7 | 47,1 |
| $Fe_2O_3/Cr_2O_3 SiO_2/BaO$ | 26,3 | 19,9 | — | 8,1 | — | 17,7 | 5,3 | — | — | 22,3 | — | 0,4 | 51,0 | 46,9 |
| $Fe_2O_3/RuO_2$ | 26,3 | 19,6 | — | 6,8 | — | 14,3 | 5,4 | — | — | 25,2 | — | 2,4 | 46,1 | 46,2 |
| $Fe_2O_3/MgO SiO_2/BeO$ | 25,5 | 21,7 | — | 6,3 | — | 15,8 | 6,8 | — | — | 23,1 | — | 0,8 | 50,6 | 47,3 |
| $FeO_3/MnO_2 K_2O$ | 26,0 | 20,8 | — | 6,4 | — | 15,1 | 6,5 | — | — | 23,3 | — | 1,9 | 48,8 | 46,3 |

TABLE 6

| | | | | | | Product composition, weight-% | | | | | | | | |
|---|---|---|---|---|---|---|---|---|---|---|---|---|---|---|
| catalyst | Ph | o-cresol | m-cresol | p-cresol | 2,5-DMP | 2,4-DMP | 2,6-DMP | 2,3-DMP | resid. DMP | 2,4,6-TMP | 2,3,6-TMP | dist. resid. | o-,p-Cr.; 2,6-DMP | phenol consumed |
| white pearls $SiO_2/Al_2O_3$ | 12,7 | 13,2 | 17,1 | 5,0 | 8,7 | 6,7 | 2,1 | 2,6 | | 1,1 | 2,7 | 28,1 | | 69,4 |
| $NiO/SiO_2 C_2O_3/K_2O$ | 35,1 | 8,6 | 1,1 | 6,1 | 2,4 | 29,5 | 0,5 | — | — | 1,2 | — | 15,5 | 15,2 | 40,7 |
| $Fe_2O_3/SiO_2$ | 32,8 | 19,6 | — | 16,9 | — | 25,3 | 2,0 | — | — | 2,7 | — | 0,7 | 38,5 | 35,3 |
| $Fe_2O_3/V_2O_5$ | 29,1 | 23,7 | — | 18,3 | — | 16,3 | 6,1 | — | — | 3,8 | — | 2,7 | 48,1 | 40,2 |
| $Fe_2O_3/B_2O_3 Cr_2O_3/BeO$ | 35,1 | 15,9 | — | 12,7 | — | 33,1 | 2,1 | — | — | 0,5 | — | 0,6 | 30,7 | 38,6 |
| $Fe_2O_3/SiO_2 Cr_2O_3/K_2O$ | 36,2 | 18,5 | — | 17,6 | — | 21,5 | 3,8 | — | — | 1,9 | — | 0,5 | 39,9 | 38,3 |
| $Fe_2O_3/SiO_2 MoO_2$ | 34,5 | 19,9 | — | 18,7 | — | 18,6 | 3,6 | — | — | 3,1 | — | 1,6 | 42,2 | 40,3 |
| $Fe_3O_4$ | 32,1 | 17,2 | — | 15,8 | — | 28,0 | 3,1 | — | — | 3,5 | — | 0,3 | 36,1 | 37,9 |
| $Fe_2O_3/SiO_2 MnO_2/CaO$ | 31,2 | 15,7 | — | 16,8 | — | 27,8 | 3,8 | — | — | 2,9 | — | 1,8 | | 37,6 |
| $Fe_2O_3/PbO Cr_2O_3/BaO$ | 30,0 | 16,7 | — | 16,1 | — | 28,5 | 3,2 | — | — | 3,4 | — | 2,1 | 36,0 | 43,1 |
| $Fe_2O_3/SiO_2 V_2O_5/BaO$ | 36,3 | 17,8 | — | 18,1 | — | 21,1 | 2,7 | — | — | 3,1 | — | 0,9 | 38,6 | 27,2 | as catalyst, characterized in that the process is carried out in the presence of a catalyst comprising iron oxide (s) or iron oxide (s) and at least one oxide selected from at least one of the groups 1. B, Al, Ce, Ga, In, Sc, Y
2. Si, Ge, Sn, Pb, Ti, Zr, Hf
3. Cr, V, Nb, Ta, Mo, W, Re, Co, Ni, Ru, Ir
4. Li, Na, K, Rb, Cs, Be, Mg, Ca, Sr, Ba, Mn, La, Cu, Zn, Cd 3. A process as claimed in claim 1 or claim 2 characterized in that the process is carried out in the liquid phase.

4. A process as claimed in claim 1 or claim 2 characterized in that the process is carried out in the presence of a catalyst, which contains at least 60 weight-% of iron oxide (s).

5. A process as claimed in claim 1 or claim 2 characterized in that the pressure range is 5–180 bar at reaction temperature.

6. A process as claimed in claim 1 or claim 2 characterized in that the temperature range is 250°–450° C.

7. A process as claimed in claim 1 or claim 2 characterized in that the residence time is 0,5–7 hours.

8. A process as claimed in claim 1 or claim 2 characterized in that the phenol added is 5–70 percent by weight of the total feed mixture.

9. A process as claimed in claim 1 or claim 2 wherein the process is carried out in an inert atmosphere.

10. A process as claimed in claim 9 wherein the inert atmosphere is hydrogen, nitrogen or a mixture thereof.

* * * * *